United States Patent [19]

Reed et al.

[11] Patent Number: 5,032,385
[45] Date of Patent: Jul. 16, 1991

[54] ORAL HYGIENE COMPOSITION

[75] Inventors: John V. Reed, Southsea; Carol A. Jeffryes, Isleworth; Peter J. Edwards, Leatherhead, all of United Kingdom

[73] Assignee: Beecham Group plc, England

[21] Appl. No.: 921,620

[22] Filed: Oct. 21, 1986

[30] Foreign Application Priority Data

Oct. 22, 1985 [GB] United Kingdom ............... 8526093

[51] Int. Cl.$^5$ ................................ A61K 7/16
[52] U.S. Cl. ..................... 424/49; 424/48; 424/52; 424/55; 424/58; 424/464; 514/718; 514/721
[58] Field of Search ............ 424/49, 52, 48, 55, 424/58, 464; 514/718, 721

[56] References Cited

U.S. PATENT DOCUMENTS

| 3,934,000 | 1/1976 | Barth | 424/49 |
| 4,022,880 | 5/1977 | Vinson | 424/55 |

FOREIGN PATENT DOCUMENTS 0161898 11/1985 European Pat. Off. .

OTHER PUBLICATIONS

Edited by J. B. Wilkinson and R. J. Moore, *Harry's Cosmeticology*, Seventh Edition, p. 612.

*Primary Examiner*—Ronald W. Griffin
*Attorney, Agent, or Firm*—Rosenman & Colin

[57] ABSTRACT

An oral hygiene composition contains (a) from 0.01 to 2% by weight of Triclosan, (b) from 2 to 10% by weight of polyethylene glycol of molecular weight from 200 to 1000, and (c) 0.1 to 2% by weight of oil-based flavor material.

The polyethylene glycol helps to maintain an effective level of orally available Triclosan.

5 Claims, No Drawings

ORAL HYGIENE COMPOSITION

The present invention relates to an oral hygiene composition containing an anti-microbial material, in particular material selected from the bis-phenol group of anti-microbials.

U.S. Pat. No 4022880 discloses the use of a particular member of the bis-phenol group of antimicrobials, 2,4,4'-trichloro-2'-hydroxydiphenyl ether, in oral hygiene formulations.

A problem associated with the use of such antimicrobials is that, due to their lipophilic nature, they tend to partition into a hydrophobic oil phase and a surfactant micellar phase and are thereby rendered unavailable for adsorption onto the oral surfaces. Since the oil/micellar phases in an oral hygiene compositions are conventionally provided by flavouring oils (such as peppermint or spearmint) and anionic detergents (such as sodium lauryl sulphate), and oils and surfactants cannot generally be removed without resulting in a product of poor consumer appeal, it would be advantageous to devise a method of making the antimicrobial available for absorption on the oral surfaces without reducing the amount of flavour or surfactant to an unacceptable level.

It has now surprisingly been found that by incorporating specified amounts of certain polyethylene glycols into oral hygiene compositions, the oral availability of antimicrobial compounds can be maintained at an effective level without severe restrictions on the quantity of oil or other hydrophobic ingredients which may be used in the composition.

According to the present invention there is provided an oral hygiene composition comprising (a) from 0.01 to 2% by weight of the composition of an antimicrobial compound of formula (I)

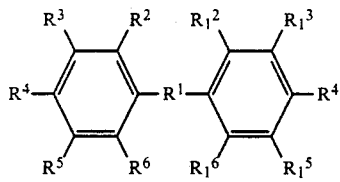

in which $R^1$ is oxygen;

each of $R^2$ to $R^6$ is hydrogen, hydroxyl alkyl and, or halogen, and each of $R^2$ to $R^6$ is hydrogen, hydroxyl alkyl and/or halogen;

(b) from 2% to 10% by weight of the composition of one or more polyethylene glycols of molecular weight from 200 to 1000, and (c) from 0.1% to 2% of oil-based flavour material, together with an orally acceptable excipient.

Preferably, the composition of the invention contains from 4 to 8%, more preferably from 5 to 7%, by weight of polyethylene glycol.

The preferred molecular weight range of polyethylene glycol is from 200 to 600, more preferably 200 to 400 and particularly about 300.

Examples of compounds of formula (I) are:
2, 4, -dichloro-2'- hydroxydiphenyl ether
4, 4, dichloro-2'- hydroxydiphenyl ether
2, 4, 4, tribromo-2'- hydroxydiphenyl ether
2,4,4,-trichloro-2'-hydroxydiphenyl ether (Triclosan)

Triclosan is a particularly preferred compound of formula (I)

The preferred weight range of compound of formula (I) is from 0.01 to 1.0%, particularly 0.1% to 0.5%.

The quantity of oil-based flavour material is not critical within the given range, but a range of about 0.5 to 1% is generally preferred. The orally acceptable excipient in the composition of the invention can include any of the well known ingredients commonly present in oral hygiene preparations, provided they are compatible with the essential ingredients of the invention. Thus, the excipient will normally include a detergent, preferably an anionic detergent such as sodium lauryl sulphate, in an amount of from 0.05 to 5%, preferably 0.5 to 3%, and particularly 0.5 to 2%, by weight of the composition.

The excipient may also contain an abrasive or polishing agent, which may include calcium carbonate, calcium phosphate, water-insoluble sodium or potassium metaphosphates, calcium pyrophosphate, aluminium trihydrate or calcium silicate.

The various forms of silica may also be used as abrasive or polishing agents, especially silica xerogels as defined in U.S. Pat. No. 3538230

Abrasives or polishing agents may be employed in a total amount of from about 10 to 90% by weight of the composition preferably from 20 to 75% by weight.

Fluoride sources may also be present in the composition of the invention, and these may include ionic fluorides, such as alkali-metal fluorides, preferably sodium fluoride, and/or ionic monofluorophosphates. A preferred ionic monofluorophosphate is an alkali-metal monofluorophosphate especially sodium monofluorophosphate.

The composition of the invention may also contain other ingredients such as humectants (for example glycerine, sorbitol and/or further glycols) gelling agents (for example natural or synthetic gums, gum tragacanth, sodium carboxymethylcellulose, polyvinyl pyrolledone or starch), sweetening agents, for example soluble sacharin, chloroform, colouring or whitening agents (for example titanium dioxide), preservatives, emulsifying agents, silicones, alcohol, menthol, chlorophyll compounds (for example sodium copper chlorophyllin), anti-plaque agents, anticalculus agents, agents for sensitive dentine (for example strontium salts, formaldehyde), and agents which enhance the anti-caries activity of fluorides (for example calcium glycerophosphate).

The compositions of the invention are preferably in the form of dentifrices, but may also take the form of compositions which will be chewed by the user, for example chewing gum, tablets, pastil les and lozenges. Such compositions will contain conventional base materials together with suitable flavours and sweetening agents and may be formulated in known manner.

The invention is now illustrated by means of the following Examples:

EXAMPLE 1

| Toothpaste Formulation | % w/w |
| --- | --- |
| Sorbitol solution (70%) | 24.00 |
| Saccharin | 0.42 |
| Triclosan | 0.20 |
| Carboxymethyl Cellulose | 0.85 |
| Natrosol 250H | 0.10 |
| Calcium silicate | 0.20 |
| Sodium monofluorophosphate (28.6%) | 2.80 |

-continued

| Toothpaste Formulation | |
|---|---|
| | % w/w |
| Calcium glycerophosphate | 0.13 |
| Chalk | 45.77 |
| Empicol | 1.00 |
| Peppermint Oil | 0.50 |
| PEG 300 | 6.00 |
| Water | 18.03 |
| TOTAL | 100.00 |

EXAMPLE 2

| Gel Toothpaste (opacified) | |
|---|---|
| | % w/w |
| Zeodent 113 | 18.00 |
| Sorbitol | 50.00 |
| Syloblanc 34 | 3.50 |
| PEG 400 | 6.00 |
| Carboxymethyl cellulose CMC 7MF | 1.00 |
| Peppermint Oil | 0.50 |
| 15% Saccharin solution | 1.20 |
| Sodium monofluorophosphate (28.6%) | 2.80 |
| Nipagin sodium | 0.15 |
| Empicol (30%) | 3.00 |
| Calcium glycerophosphate | 0.07 |
| Natrosol 250H | 1.50 |
| Triclosan | 0.20 |
| Water | 11.93 |
| TOTAL | 100.00 |

Zeodent is a trade mark of the Huber Corporation
Syloblanc is a trade mark of W. R. Grace & Co.
Empicol is sodium lauryl sulphate
Natrosol is a trade mark of Hercules Ltd.

DEMONSTRATION OF EFFECTIVENESS

Materials

The following test mixture A was made up by normal admixture of the ingredients:

| Mixture A | |
|---|---|
| [1]Irgasan DP 300 | 0.20 |
| Sodium Lauryl sulphate | 1.00 |
| Peppermint Oil | 0.50 |
| Sodium hydroxide | 0.25 |
| Sorbitol (70%) | 30.00 |
| Water | 25.00 |

A 1:6 dilution of the above with sterile deionised water was considered to be representative of the slurry formed in the oral cavity during brushing with a typical toothpaste formulation.
[1]Trade mark of Ciby Geigy for Triclosan Mixture A was modified by incorporating therein PEG 300 (polyethylene glycol of M.W. ca 300) in amounts of from 4% to 8% by weight, in 0.5% increments.

PROCEDURE

Test

Hydroxyapatitic discs, prepared by the method of Forward (Forward G. C. Caries Res. 11, 9–15, 1976) were incubated in sterile human saliva overnight at 37° C. After 1 minute rinsing in sterile deionised water, triplicate discs were treated for 1 minute with 1.6 dilutions of the various mixtures. Discs exposed for 1 minute to a series of standard solutions containing 50–300 ppm Irgasan DP300 were similarly treated.

Three one minute rinses with sterile deionised water were employed to eliminate the effects of any carried-over, unadsorbed anti microbial.

Irgasan adsorption was assessed by agar diffusion, the rinsed discs being placed, treated surface downwards, onto the surface of assay plates containing Brain Heart Infusion agar seeded with approximately $10^6$ cfu/ml Staphylococcus aureus ATCC 6548. Plates were incubated aerobically for 24 hours at 37° C., and the resulting zone diameter measured.

The Irgasan availability of each solution was determined by interpolation from the standard curve.

Results

The effect of PEG 300 on the availability of Irgasan in the various mixtures is summarized in the following Table:

| EFFECT of PEG 300 on the availability of Irgasan | | | | | |
|---|---|---|---|---|---|
| | Available Irgasan (ppm) | | | | |
| % PEG 300 | .1 | 2 | 3 | 4 | Mean |
| 4.0 | 148 | 96 | 94 | 92 | 108 |
| 4.5 | 159 | 109 | 108 | 105 | 123 |
| 5.0 | 170 | 127 | 124 | 120 | 135 |
| 5.5 | 187 | 149 | 140 | 162 | 160 |
| 6.0 | 208 | 191 | 181 | 194 | 194 |
| 6.5 | 187 | 161 | 199 | 182 | 182 |
| 7.0 | 167 | 146 | 167 | 160 | 160 |
| 7.5 | 156 | 128 | 154 | 146 | 146 |
| 8.0 | 152 | 120 | 147 | 136 | 139 |
| 0.2% Irgasan/ 0.5% Peppermint Oil 1.00% SLS system minus PEG (control) | 112 | 88 | 90 | 82 | 93 |

The available Irgasan from a control formulation without PEG 300 was also measured (control contained 0.2% Irgasan, 0.5% Peppermint oil and 1% SLS).

The results show that from 4% to 8% of PEG provided enhanced Irgasan availability, with a peak valve occurring around 6%. The level of available Irgasan was shown to be significantly greater than that in the control formulation, which did not contain PEG 300.

We claim:

1. An oral hygiene composition comprising (a) from 0.01 to 2% by weight of a composition of an antimicrobial compound of formula (I) as the active therapeutic agent

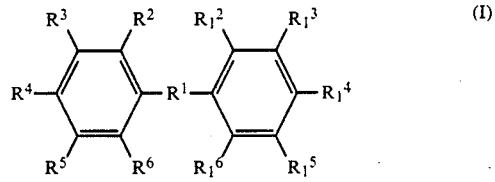

in which $R^1$ is oxygen; each of $R^2$ and $R^6$ is a substituent selected from the group consisting of hydrogen, hydroxyl, alkyl and halogen, and each of $R^2$, to $R^6$, is a substituent selected from the group consisting of hydrogen, hydroxyl, alkyl and halogen;

(b) an amount of one or more polyethylene glycols of molecular weight from 200 to 1000 sufficient to increase the oral availability of the antimicrobial compound, said amount being from 2% to 10% by weight of the composition; and (c) from 0.1% to 2% of oil-based flavour material, in combination with an orally acceptable excipient.

2. A composition according to claim 1, which contains from 4 to 8% by weight of polyethylene glycol.

3. A composition according to claim 1 in which the polyethylene glycol has a molecular weight range of from 200 to 600.

4. A composition according to claim 1, in which the compound of formula (I) is selected from the group consisting of
2, 4, -dichloro-2'-hydroxydiphenyl ether
4, 4' dichloro-2'-hydroxydiphenyl ether and
2, 4, 4' tribromo-2'-hydroxydiphenyl ether.

5. A composition according to claims 1, which includes from 0.05 to 5% by weight of detergent.

* * * * *